United States Patent
Palpu et al.

(10) Patent No.: US 7,247,322 B2
(45) Date of Patent: Jul. 24, 2007

(54) HERBAL NUTRITIOUS CHOCOLATE FORMULATION AND PROCESS FOR PREPARATION THEREOF

(75) Inventors: Pushpangadan Palpu, Lucknow (IN); Ajay Kumar Singh Rawat, Lucknow (IN); Chandana Venkateswara Rao, Lucknow (IN); Sanjeev Kumar Ojha, Lucknow (IN); Gaddam Dayanand Reddy, Lucknow (IN)

(73) Assignee: Council of Scientific and Industrial Research, New Delhi, IN (US)

( * ) Notice: Subject to any disclaimer, the term of this patent is extended or adjusted under 35 U.S.C. 154(b) by 0 days.

(21) Appl. No.: 11/024,020

(22) Filed: Dec. 28, 2004

(65) Prior Publication Data

US 2006/0141066 A1    Jun. 29, 2006

(51) Int. Cl.
*A61K 36/00* (2006.01)

(52) U.S. Cl. .................................................. 424/725
(58) Field of Classification Search .................. None
See application file for complete search history.

(56) References Cited

U.S. PATENT DOCUMENTS 5,693,327 A * 12/1997 Shah .......................... 424/734
5,886,029 A *  3/1999 Dhaliwal ..................... 514/456

* cited by examiner

*Primary Examiner*—Christopher R. Tate
*Assistant Examiner*—Melenie McCormick
(74) *Attorney, Agent, or Firm*—Ladas and Parry LLP

(57) ABSTRACT

The present invention provides a novel herbal chocolate composed of *Tinospora cordifolia*, *Glycyrrhyza glabra*, *Adhatoda vasica*, *Madhuca indica* and *Cassia occidentalis*. The solid or semisolid nutritious composition is rich in protein/mineral fortified with standardized herbs with proven pharmacological activities such as anti-oxidant, anti stress and adaptogenic property and relief the chronic cough and cold.

36 Claims, No Drawings

HERBAL NUTRITIOUS CHOCOLATE FORMULATION AND PROCESS FOR PREPARATION THEREOF

FIELD OF INVENTION

The present invention relates to development of chocolate with novel herbal composition(s) with proven pharmacological activities such as anti-oxidant, anti stress, adaptogenic and immune enhancing property.

BACKGROUND AND PRIOR ART OF THE INVENTION

The origins of chocolate can be traced back to ancient Maya and Aztec civilizations in Central America, who first enjoyed 'chocolate; a much-prized spicy drink made from roasted cocoa beans. Chocolate was exclusively for drinking until the early Victorian era, when a technique for making solid 'eating' chocolate was devised. Throughout its history, whether as a cocoa, a drinking chocolate beverage or confectionery treat, chocolate has been a much sought after food.

Conventional chocolate is assumed to be a causative factor of to migraines, acne and pimples, diabetes and obesity and also considered a luxury food. On the other hand Cocoa beans contain a type of antioxidant that may have a role in the prevention of certain diseases. The catechins found in cocoa beans aid resistance against degenerative diseases such as cancer and heart disease. It is therefore desirable to provide a chocolate type of edible substance, which can provide positive effects with lesser or no side effect. One of the methods by which this can be achieved is by blending of modern knowledge with traditional Indian systems of medicine and preparing medicine in the form of food, which is therapeutically effective. Another factor, which was considered in the present investigation, was to ensure that the costs of the process were not prohibitive.

OBJECTS OF THE INVENTION

The main object of the present invention to provide a novel herbal nutritious chocolate and a process for preparation thereof.

SUMMARY OF THE INVENTION

The present invention provides chocolate based herbal nutritious formulation, comprising extracts obtained from *Tinospora cordifolia, Glycyrrhyza glabra, Adhatoda vasica, Madhuca indica* and *Cassia occidentalis* and mixed with acceptable additives.

In one embodiment of the invention the extracts are in the form of juices.

In another embodiment of the invention the extracts/juice of the plants are mixed in the ratio consisting of *Tinospora cordifolia* 4-7%, *Glycyrrhyza glabra* 4-7%, *Adhatoda vasica* 4-7%, *Madhuca indica* 8-15%, and *Cassia occidentalis* 2-4%.

In another embodiment of the invention, the formulation is in the form of a semisolid, solid or granules.

In another embodiment of the invention, the extracts of plants are selected from alcoholic extracts, aqueous extracts and mixtures thereof.

In another embodiment of the invention, the alcoholic extracts are ethanolic extracts.

In another embodiment of the invention, the plant extract is used in an amount of 20-40% wt of the total formulation.

In another embodiment of the invention, the additives are selected from the group consisting of starch, lactose, sugar, gum acacia, lubricants and any mixture thereof.

In another embodiment of the invention, the plant extracts are obtained from plant parts selected from the group consisting of leaf, seeds, floral parts rhizome, aerial parts and any combination thereof.

In another embodiment of the invention, the lubricant is milk or a milk derivative.

The present invention also relates to a method for preparation of a chocolate based herbal nutritious composition comprising extracts obtained from *Tinospora cordifolia, Glycyrrhyza glabra, Adhatoda vasica, Madhuca indica* and *Cassia occidentalis* and mixed with acceptable additives, the method comprising:

a) selecting parts of the plant to be extracted;
b) drying the plant parts in shade;
c) powdering the dried plant parts to a coarse powder;
d) preparing a decoction from the plant parts by sieving the coarsely powdered plant material, adding an extracting agent and boiling to obtain a concentrate;
e) adding *Madhuca indica* (floral parts) and roasted seeds of *Cassia occidentalis* to the concentrate, followed by spray drying additives thereon;
f) heating mixture obtained in step (e) gently to form a paste of desired consistency and transferring the paste to molds and cooling to obtain a solid or semisolid formulation.

In one embodiment of the invention the extracts are in the form of juices.

In another embodiment of the invention the extracts/juice of the plants are mixed in the ratio consisting of *Tinospora cordifolia* 4-7%, *Glycyrrhyza glabra* 4-7%, *Adhatoda vasica* 4-7%, *Madhuca indica* 8-15%, and *Cassia occidentalis* 2-4%.

In another embodiment of the invention, the formulation is in the form of a semisolid, solid or granules.

In another embodiment of the invention, the extracts of plants are selected from alcoholic extracts, aqueous extracts and mixtures thereof.

In another embodiment of the invention, the alcoholic extracts are ethanolic extracts.

In another embodiment of the invention, the plant extract is used in an amount of 20-40% wt of the total formulation.

In another embodiment of the invention, the additives are selected from the group consisting of starch, lactose, sugar, gum acacia, lubricants and any mixture thereof.

In another embodiment of the invention, the plant extracts are obtained from plant parts selected from the group consisting of leaf, seeds, floral parts, rhizome, aerial parts and any combination thereof.

In another embodiment of the invention, the lubricant is milk or a milk derivative.

In another embodiment of the invention, the molding is carried out by cooling the paste in molds at a temperature in the range of −4 to −20° C.

In another embodiment the formulation is stored at room temperature.

In another embodiment of the invention, the formulation has a shelf life of 2 years.

In another embodiment, the formulation exhibits antioxidant activity.

In another embodiment, the formulation exhibits adaptogenic activity.

In another embodiment, the formulation exhibits anti-stress activity.

In yet another embodiment, the formulation exhibits enzymatic super oxide dismutase enhancing activity.

In another embodiment, the formulation exhibits lipid peroxidation inhibition.

In another embodiment, the formulation exhibits enzymatic enhancing catalase activity.

In another embodiment, the formulation exhibits enhanced protein content.

DETAILED DESCRIPTION OF THE INVENTION

The present invention provides a novel herbal nutritious composition useful in the treatment of anti fatigue, anti stress agent and provides vitality and energy. The novel herbal nutritious composition comprises of decoction of *Tinospora cordifolia, Glycyrrhyza glabra, Adhatoda vasica*, and paste of *Madhuca indica* with roasted seeds of *Cassia occidentalis*. In a battery of tests like hypoxia and swimming endurance the synergistic effect of the composition showed 90% potency confirms the adaptogenic activity. The plants used in the invention are reported to possess the following properties.

*Tinospora cordifolia* Family: Menispermnaceae

Botanical Descriptions: A large glabrous climbing shrub. Stems rather succulent with long filiform, aerial roots arising from branches. Bark; warty, papery thin, creamy white or grey brown. Peels off easily. Wood, soft, perforated. Leaves; membranous, cordate with broad sinus. Pointed at the tip. Flowers; unisexual and greenish, in long clusters. Seeds; curved. Drupes; ovoid, succulent, lustrous, red, pea sized. Fruits; fleshy, one seeded. Flowers during the summer and fruits during the winter. It is found throughout tropical India, ascending to an altitude of 300 m.

Medicinal Uses: Useful in bilious fever, rheumatism, general debility, seminal weakness, splenic diseases and urinary affections. Fresh plant is considered more efficacious. It is mostly used for preparing a kind of starch known as Guduchi satva or Sat giloe.

Phytochemistry: Sesquiterpene tinocordifolin, sesquiterpene glucoside tinocordifolioside, tinosponone, tinocordioside, cordioside, furanoid diterpenes, a new clerodane furanoditerpene viz. columbin, tinosporaside, an immunologically active arabinogalactan, two phytoecdyyones viz., ecdysterone and makisterone and several glycosides isolated as polyacetates. Other alkaloids viz., jatrorrhizine, palmatine, berberine, tembeterine, phenylpropene disaccharides cordifolioside A, B and C, choline, tinosporic acid, tinosporal, tinosporon, 20-β-hydroxyecdysone, palmatoside C and F, cordifolisides D and E, diterpenoid furanolactones.

Pharmacology: The water and ethanolic extract inhibited the cyclophosphamide induced immunosupression. Aqueous extract of the stem showed anti-inflammatory, analgestic and antipyretic properties in rats. In clinical studies, it also showed immunosuppressive effect in obstructive jaundice patients, antioxidant activity and amelioration of cylcophosphamide-induced toxicity.

*Glycyrrhyza glabra* Family: Papilionaceae,Fabaceae.

Botanical Description: A perennial herbs and under shrubs distributed in the sub-tropical and warm temperate regions of the world, chiefly in the Mediterranean countries and china. The drug is imported into India on a considerable scale from Asia Minor, Iraq, Persia and other Central Asian countries.

Phytochemistry: Glycyrrhizin, Glycyrrhizic acid, and glycyrrhetinic acid , the characterstic sweet taste is due to Glycyrrhizin (2-14%).

Pharmacology: Rhizomes and roots tonic, expectorant, demulcent, and laxative, used for allaying coughs and catarrhal affections, and irritable conditions of the membranes of the urinary organs.

*Madhuca indica* (Koenig) Gmelin Family: Sapotaceae

Botanical Description: A medium sized to large deciduous tree, leaves clustered near the ends of stout branches 5-25 cm long and 3.5-12 cm wide, apex shortly acuminate, base rounded to cuneate; petioles 2-4 cm long; stipules 0.6-1 cm long, subulate, densely pubescent. Flowers numerous, scented, clustered on leafless shoots; fruits ovoid or subglobose, 2.5-5 cm long, greenish turning reddish-yellow or orange when ripe, fleshy; seeds 1-4, brown or ochre, oblong-ellipsoid, shiny, 2.5-3.8 cm long and 1.5 cm wide. Flowers appear with new leaves from February to April and fruits ripen from May to August in northern and central India.

Pharmacology: The seed oil has emollient properties and is useful for external application in treating skin diseases, rheumatism and headache. It is also laxative and used to treat chronic constipation, piles and haemorrhoids and is sometimes used as an emetic and galactagogue. The ground flowers are applied as a paste to relieve aching muscles. The bark is used for treating rheumatism, ulcers, itches, bleeding and spongy gums, tonsillitis and diabetes mellitus. The roots are applied externally to promote healing of ulcers.

*Cassia occidentalis* (L) Family: Caesalpiniaceae

Botanical Description: An erect fetid, woody herb or undershrub, 60-150 cm tall, with a smooth, purplish or green stem. Leaves alternate, pinnate, 15-20 cm long, stipulate with a sessile dark brown gland near the base of the petiole; leaflets 3-5 pairs, opposite, short-stalked, membranous, ovate or lanceolate, 3-9 cm long and 1.5-4 cm wide, base rounded, apex acute or attenuate, glabrous above glaucous beneath. Flowers yellow, in short, few flowered axillary or terminal recemes. Flowers and fruits throughout the year depending on locality, but mainly between August and January in central India.

Phytochemistry: The seeds contain tannic acid, mucilage (36%), fatty acid (2.56%), emodin and a toxalbumin. Chrysarobin (methyl-di hydroxy anthranol. M. P. 203-4° C.) has been isolated from the benzene extract of the seeds. The fatty oil contains: saturated fatty acids 19.7; linoleic acid, 31.4; oleic acid 30.7, linolenic acid, 6.3;volatile constituents, 0.7; un sapon matter 7.4%.

Pharmacology: All parts of the plant have similar medicinal properties and are considered purgative, tonic, febrifugal, expectorant and diuretic. The plant is used as a vermifuge and to treat sore eyes, haematuria, rheumatism, dropsy, typhoid, asthma, blood disorders and is reportedly effective against leprosy. A decoction of the plant is used for the treatment of hysteria, dysentery and other stomach troubles. The roots are considered bitter, tonic, purgative, anthelmintic and diuretic. In ayurveda a paste made from the roots is considered specific ringworm and other skin ailments. The leaves are also used externally to relieve inflammatory swellings, rheumatism, wounds and sprains. The root bark is used as a quinine substitute to cure fever, and its decoction is used as a stimulant and as a specific medicine for gonorrhoea and hepatic troubles.

The herbal nutritious chocolate of the invention is useful as a nutrient source and comprises extracts obtained from *Tinospora cordifolia, Glycyrrhyza glabra, Adhatoda vasica, Madhuca indica* and *Cassia occidentalis* with acceptable additives. The formulation is useful in the field of foods and pharmaceuticals as a nutrient source. The extracts/juice of the plants are mixed in the ratio viz. *Tinospora cordifolia* (4-7%), *Glycyrrhyza glabra* (4-7%), *Adhatoda vasica* (4-7%), *Madhuca indica* (8-15%), and *Cassia occidentalis* (2-4%). The composition is in conventional form of a semisolid/solid/granules or any other form.

The extracts of plants may be alcoholic or aqueous extract or mixture thereof. The alcohol used is preferably ethanol. The formulation comprises plant extract about 20-40% wt of the total formulation. The additives used are conventional additives such as starch, lactose, sugar, gum acacia and known lubricant such as milk or milk derivatives or mixture thereof.

The plant extracts are obtained from plant parts selected from leaf, seeds, floral parts rhizome and aerial parts or any combination thereof.

The method of preparation of the formulation comprises
(a) selecting parts of medicinal plants from a group comprising leaves, rhizome and aerial parts including flowers,
(b) drying the plant material in shade,
(c) powdering the dried plant material to a coarse powder,
(d) preparation of decoction: the coarsely powdered plant material was sieved and added water and boiled to concentrate,
(e) adding *Madhuca indica* (fl.parts) and roasted seeds of *Cassia occidentalis* to the concentrate followed by spray drying milk, Sugar and Gum acacia,
(f) heating the above gently, and after proper consistency is attained keeping the paste in molds and cooling at a temperature ranging from −4 to −20° C. to obtain solid or semisolid.

The formulation obtained can be stored at room temperature and has a shelf life of 2 years. The various properties exhibited by the formulation include potent antioxidant activity, potent adaptogenic activity, potent anti-stress activity, potent enzymatic super oxide dismutase enhancing activity, potent lipid peroxidation inhibition, potent enzymatic enhancing catalase activity. The herbal nutritious composition also shows an enhanced protein content. The herbal nutritious composition helpful in defending the body against the effects of stressful environment and provide vitality and energy.

The following examples are illustrative of the invention and should not be construed as limiting the scope of the invention in any manner.

Formulatioin1 (F1):

| | |
|---|---|
| 1. *Tinospora cordifolia* (stem) | 7% |
| 2. *Adhatoda vasica* (Wl. Pl.) | 0% |
| 3. *Glycyrrhyza glabra* (Rhizome) | 0% |
| 4. *Madhuca indica* (fl.parts) | 14% |
| 5. *Cassia occidentalis* | 3% |
| 6. Spray dried milk powder | 10% |
| 7. Sugar | 10% |
| 8. Gum *acacia* powder | 1% |
| 9. Lactose | to make up 100% |

Formulatioin2 (F2):

| | |
|---|---|
| 1. *Tinospora cordifolia* (stem) | 0% |
| 2. *Adhatoda vasica* (Wl. Pl.) | 6% |
| 3. *Glycyrrhyza glabra* (Rhizome) | 0% |
| 4. *Madhuca indica* (fl.parts) | 12% |
| 5. *Cassia occidentalis* | 3% |
| 6. Spray dried milk powder | 10% |
| 7. Sugar | 10% |
| 8. Gum *acacia* powder | 1% |
| 9. Lactose | to make up100% |

Formulatioin3 (F3):

| | |
|---|---|
| 1. *Tinospora cordifolia* (stem) | 0% t |
| 2. *Adhatoda vasica* (Wl. Pl.) | 0% |
| 3. *Glycyrrhyza glabra* (Rhizome) | 7% |
| 4. *Madhuca indica* (fl.parts) | 14% |
| 5. *Cassia occidentails* | 3% |
| 6. Spray dried milk powder | 10% |
| 7. Sugar | 10% |
| 8. Gum *acacia* powder | 1% |
| 9. Lactose | to make up100% |

Formulatioin4 (F4):

| | |
|---|---|
| 1. *Tinospora cordifolia* (stem) | 6% |
| 2. *Adhatoda vasica* (Wl. Pl.) | 6% |
| 3. *Glycyrrhyza glabra* (Rhizome) | 6% |
| 4. *Madhuca indica* (fl.parts) | 12% |
| 5. *Cassia occidentalis* | 3% |
| 6. Spray dried milk powder | 9% |
| 7. Sugar | 9% |
| 8. Gum *acacia* powder | 1% |
| 9. Lactose | to make up100% |

The above (1,2,3) dried material coarsely powdered with 16× screen and water is added which is heated on to concentrate. Out of which 300 ml of decoction is taken in it of *Madhuca indica* (fl.parts) added along with powder of roasted seeds of *Cassia occidentalis* followed by spray dried milk and gum acacia. Mixed properly through mixer, and sieved through fine mesh no. 60, and consistency to paste is kept in molds and in oven to remove excess of moisture. Altering the first three ingredients, and taking them altogether has provided four sets of combination.

TABLE 1

Effect of formulation on chronic stress-induced changes in lipid peroxidation, superoxide dismutase and catalase in rats.

| S.No | Treatment groups (mg/kg, p.o.) | Lipid peroxidation (nmoles of TBARS) | Superoxide dismutase | Catalase |
|---|---|---|---|---|
| 1 | Vehicle | 0.45 ± 0.02 | 105.3 ± 11.2 | 33.9 ± 2.4 |
| 2 | Vehicle + stress | 0.71 ± 0.04 | 256.8 ± 7.5 | 19.5 ± 1.9 |
| 3 | F1 | 0.51 ± 0.02 | 235.6 ± 6.9 | 22.7 ± 3.1 |
| 4 | F2 | 0.48 ± 0.02 | 201.3 ± 5.1 | 25.3 ± 2.7 |
| 5 | F3 | 0.39 ± 0.02$^a$ | 185.6 ± 6.9$^b$ | 26.7 ± 3.1 |
| 6 | F4 | 0.28 ± 0.02$^c$ | 162.3 ± 5.1$^c$ | 31.3 ± 2.7$^a$ |

Values are mean ± S.E.M.
P: [a]<0.05, [b]<0.01 and [c]<0.001 compared to respective control group.
NOTE:

TABLE 1-continued

Effect of formulation on chronic stress-induced changes in lipid peroxidation, superoxide dismutase and catalase in rats.

| S.No | Treatment groups (mg/kg, p.o.) | Lipid peroxidation (nmoles of TBARS) | Superoxide dismutase | Catalase |
|---|---|---|---|---|

No mortality was found in any of the treated group.
No gross abnormality in behavior was observed in the animal exposed with herbal preparation.

Formulation (F1) consisted of only extract of *Tinospora cordifolia* (stem) Formulation (F2) consisted of only extract *Adhatoda vasica* (Wl. Pl.) Formulation (F3) consisted of only *Glycyrrhyza glabra* (Rhizome) where as Formulation (F4) consisted of all the above.

Table 1 shows that herbal formulation F4 has potent antioxidant activity as evidenced by its ability to prevent lipid peroxidation from 0.71 to 0.28 and by the augmentation of the antioxidant enzymes viz. superoxide dismutase (256.8 in vehicle under stress to 162.3 at F4) and catalase (19.5 in vehicle under stress to 31.3 at F4) when compared to the vehicle which is plain water. Thus the herbal formulation prepared exhibits potent antioxidant activity under stress conditions and hence is a good rejuvenator.

Lipid Peroxidation: The fundic part liver was homogenized (5%) in ice-cold 0.9% NaCl in glass homogenizer for 30 s. The homogenate was centrifuged for 10 min A volume of the homogenate (0.20 ml) was transferred to a vial and was mixed with 0.2 ml of a 8.1% (w/v) sodium dodecyl sulfate solution, 1.50 ml of a 20% acetic acid solution (adjusted to pH 3.5 with NaOH) and 1.50 ml of a 0.8% (w/v) solution of thiobarbituric acid (TBA) and the final volume was adjusted to 4.0 ml with distilled water. Each vial was tightly capped and heated in a boiling water bath for 60 min. The vials were then cooled under running water. Equal volumes of tissue blank or test samples and 10% trichloroacetic acid were transferred into a centrifuge tube and centrifuged. The absorbance of the supernatant fraction was measured at 532 nm. Control experiment was processed using the same experimental procedure except the TBA solution was replaced with distilled water. 1,1,3,3-Tetraethoxypropan was used as standard for calibration of the curve and is expressed as nanomoles per milligram protein.

SOD and Catalase:

Decomposition of $H_2O_2$ in presence of catalase (CAT) was followed at 240 nm. One unit (U) of catalase was defined as the amount of enzyme required to decompose 1 µmol of $H_2O_2$ per minute, at 25° C. and pH 7.0. Results are expressed as units of CAT activity per milligram of protein. Superoxide dismutase (SOD) activity was estimated by the inhibition of nicotinamide adenine dinucleotide (reduced)-phenazine methosulphate-nitrobluetetrazolium reaction system. One unit of the enzyme is equivalent to 50% inhibition in the formazan formation in 1 min at room temperature (25° C.) and the results have been expressed as units of SOD activity per milligram of protein.

TABLE 2

Effect of formulation on hypoxia and swimming performance time in mice.

| S.No | Treatment | Dose (mg/kg, p.o) | Hypoxia time | Swimming endurance |
|---|---|---|---|---|
| 1. | Control + stress | — | 22.34 ± 1.15 | 236.21 ± 25.11 |
| 2. | F1 | 200 | 28.11 ± 1.55 | 295.12 ± 27.41 |
| 3. | F2 | 200 | 31.54 ± 2.11 | 325.45 ± 27.05 |
| 4. | F3 | 200 | 40.01 ± 2.68 | 366.52 ± 26.74 |
| 5. | F4 | 200 | 45.89 ± 3.05[a] | 423.21 ± 28.85[a] |
| 6. | Commercially available sample | 200 | 24.35 ± 2.1 | 246.25 ± 23.18 |

Values are mean ± S.E.M.
P: [c]<0.001 compared to respective control group.
NOTE:
No mortality was found in any of the treated group.
No gross abnormality in behavior was observed in the animal exposed with herbal preparation.

Formulation (F1) consisted of only extract of *Tinospora cordifolia* (stem) Formulation (F2) consisted of only extract *Adhatoda vasica* (Wl. Pl.) Formulation (F3) consisted of only *Glycyrrhyza glabra* (Rhizome) where as Formulation (F4) consisted of all the above.

As evident from Table 2 herbal formulation F4 exhibits potent adaptogenic activity as evident from increase in hypoxia time from 28.11 under stress to 45.89 upon administration of F4 and increase in swimming endurance from 295.12 to 423.21 upon administration of F4.

Commercially available sample did not significant activity in hypoxia time and swimming endurance tests of the adaptogenic activity.

Procedures for Adaptogenic Activity

Hypoxia Time:

The animals were placed in an empty glass jar of 300 mL capacity attached with an electronic watch. The jars were made airtight with greased glass stoppers and time until the onset of convulsion was recorded (Singh B et al, 2001, Phytotherapy Research, 15; 311-318).

Swimming Performance Time:

The animals were allowed to swim inside Perspex glass beaker (30 cm high with 20 cm diameter containing water up to 25 cm high) maintained at 26°±1° C. with a continuous air current from the bottom. The end point of swimming endurance was taken as when the mice remained at the bottom for more than 10s (Singh B et al, 2001, Phytotherapy Research, 15; 311-318).

We claim:

1. A nutritious composition, comprising extracts obtained from *Tinospora cordifolia*, *Glycyrrhyza glabra*, *Adhatoda vasica*, *Madhuca indica* and *Cassia occidentalis*.

2. The composition as claimed in claim 1 further comprising one or more physiologically acceptable additives.

3. The composition according to claim 1 wherein the extracts are in the form of juices.

4. The composition as claimed in claim 2 wherein the extracts are mixed in a proportion of 4-7% *Tinospora cordifolia*, 4-7% *Glycyrrhyza glabra*, 4-7% *Adhatoda vasica*, 8-15% *Madhuca indica* and 2-4% *Cassia occidentalis*.

5. The composition as claimed in claim 1 which is a solid, semisolid or in the form of granules.

6. The composition as claimed in claim 2 which is a solid, semisolid or in the form of granules.

7. The composition as claimed in claim 2 wherein the extracts are selected from alcoholic extracts, aqueous extracts or mixtures thereof.

8. The composition as claimed in claim 7 wherein the alcoholic extracts are ethanolic extracts.

9. The composition as claimed in claim 2 wherein the extracts comprise 20-40% wt of the composition.

10. The composition as claimed in claim 2 wherein the one or more additives are selected from the group consisting of starch, lactose, sugar, gum acacia, and lubricants or a mixture thereof.

11. The composition as claimed in claim 10 wherein the lubricant is milk or a milk derivative.

12. The composition as claimed in claim 2 wherein the extracts are obtained from plant parts selected from the group consisting of leaf, seeds, floral parts, rhizome, and aerial parts or a mixture thereof.

13. A method for preparation of a nutritious composition comprising extracts obtained from *Tinospora cordifolia, Glycyrrhyza glabra, Adhatoda vasica, Madhuca indica* and *Cassia occidentalis* and mixed with one or more physiologically acceptable additives, comprising the steps of:
(a) selecting parts of *Tinospora cordifolia, Glycyrrhyza glabra*, and *Adhatoda vasica* to be extracted;
(b) drying the parts in shade;
(c) powdering the dried parts to form a coarse powder;
(d) sieving the coarse powder to prepare a decoction, adding an extracting agent and boiling to obtain a concentrate;
(e) adding floral parts of *Madhuca indica* and roasted seeds of *Cassia occidentalis* to the concentrate, spray drying one or more additives thereon to form a mixture; and
(f) heating the mixture obtained in step (e) gently to form a paste.

14. A method for preparation of a nutritious composition comprising extracts obtained from *Tinospora cordifolia, Glycyrrhyza glabra, Adhatoda vasica, Madhuca indica* and *Cassia occidentalis* and mixed with one or more physiologically acceptable additives, comprising the steps of:
(a) powdering dried parts of *Tinospora cordifolia, Glycyrrhyza glabra*, and *Adhatoda vasica* to form a coarse powder;
(b) sieving the coarse powder to prepare a decoction, adding an extracting agent and boiling to obtain a concentrate;
(c) adding floral parts of *Madhuca indica* and roasted seeds of *Cassia occidentalis* to the concentrate, spray drying one or more additives thereon to form a mixture; and
(d) heating the mixture obtained in step (c) gently to form a paste.

15. The method according to claim 13 wherein the paste is transferred to a mold and cooled to obtain a solid or semi-solid composition.

16. The method according to claim 14 wherein the paste is transferred to a mold and cooled to obtain a solid or semi-solid composition.

17. The method according to claim 13 wherein the paste is used to form granules.

18. The method as claimed in claim 13 wherein the extracts are in the form of juices.

19. The method as claimed in claim 13 wherein the extracts are mixed in a proportion of 4-7% *Tinospora cordifolia*, 4-7% *Glycyrrhyza glabra*, 4-7% *Adhatoda vasica*, 8-15% *Madhuca indica* and 2-4% *Cassia occidentalis*.

20. The method as claimed in claim 13 wherein the extracts are selected from alcoholic extracts, aqueous extracts or mixtures thereof.

21. The method as claimed in claim 20 wherein the alcoholic extracts are ethanolic extracts.

22. The method as claimed in claim 13 wherein the extract comprises 20-40% wt of the composition.

23. The method as claimed in claim 13 wherein the one or more additives are selected from the group consisting of starch, lactose, sugar, gum acacia, and lubricants or a mixture thereof.

24. The method as claimed in claim 23 wherein the lubricant is milk or a milk derivative.

25. The method as claimed in claim 13 wherein the extracts are obtained from plant parts selected from the group consisting of leaf, seeds, floral parts, rhizome, aerial parts and a mixture thereof.

26. The method as claimed in claim 20 wherein the molding is carried out by cooling the paste in molds at a temperature in the range of −4 to −20° C.

27. The composition as claimed in claim 1 wherein the composition is shelf stable at room temperature.

28. The composition as claimed in claim 1 wherein the composition has a shelf life of 2 years.

29. The composition as claimed in claim 2 wherein the composition is shelf stable at room temperature.

30. The composition as claimed in claim 2 wherein the the composition has a shelf life of 2 years.

31. The composition as claimed in claim 1 wherein the composition exhibits antioxidant activity.

32. The composition as claimed in claim 1 wherein the composition exhibits adaptogenic activity.

33. The composition as claimed in claim 1 wherein the composition exhibits anti-stress activity.

34. The composition as claimed in claim 1 wherein the composition exhibits enzymatic superoxide dismutase enhancing activity.

35. The composition as claimed in claim 1 wherein the composition exhibits lipid peroxidation inhibition.

36. The composition as claimed in claim 1 wherein the composition exhibits enzymatic enhancing catalase activity.

* * * * *

UNITED STATES PATENT AND TRADEMARK OFFICE
CERTIFICATE OF CORRECTION

PATENT NO. : 7,247,322 B2 Page 1 of 1
APPLICATION NO. : 11/024020
DATED : July 24, 2007
INVENTOR(S) : Pushpangadan Palpu et al.

It is certified that error appears in the above-identified patent and that said Letters Patent is hereby corrected as shown below:

On title page, item 73, delete "(US)"

Signed and Sealed this

Second Day of October, 2007

JON W. DUDAS
*Director of the United States Patent and Trademark Office*